United States Patent [19]

Rasure

[11] 4,117,840

[45] Oct. 3, 1978

[54] PEDIATRIC RESTRAINT GARMENT

[76] Inventor: Rebecca Ann Rasure, Rte. No. 5 Cedar La., Rome, Ga. 30161

[21] Appl. No.: 779,982

[22] Filed: Mar. 22, 1977

[51] Int. Cl.$^2$ ............................................. A61F 13/00
[52] U.S. Cl. ........................................... 128/134; 2/69
[58] Field of Search .................... 128/133, 134; 2/69.5, 2/69, 64, 75, 114

[56] References Cited

U.S. PATENT DOCUMENTS

| 2,034,954 | 3/1936 | Murphy | 128/134 |
| 2,423,392 | 7/1947 | Krogh | 128/134 |
| 2,652,052 | 9/1953 | Smith | 128/134 |
| 2,675,557 | 4/1954 | Kempner | 128/134 |
| 3,136,311 | 6/1964 | Lewis | 128/134 |
| 3,181,530 | 5/1965 | Storey | 128/134 |
| 3,861,666 | 1/1975 | Nishiyama et al. | 128/134 |

Primary Examiner—Lawrence W. Trapp
Attorney, Agent, or Firm—Clarence A. O'Brien; Harvey B. Jacobson

[57] ABSTRACT

A garment for restraining movement of a wearer, particularly a pediatric patient, and for securing the wearer to a bed, lounge chair, chair, or other body supporting structure, the invention comprises a one piece flexible body panel having an aperture centrally formed therein for receiving the head of the wearer, body portions of the panel adjacent the aperture being draped respectively over the posterior and anterior portion of the torso of the wearer and separably fastened together along lower portions thereof to form a jacket-like article of clothing which can be donned or removed without requiring the patient to bend or move his arms such as is normally required when placing arms through armholes in a garment. Restraining straps connected to the upper portion of the garment near the neck-receiving aperture extend parallel to the longitudinal axis of the body of the wearer and connect to the bed or other supporting structure to inhibit movement longitudinally of said bed. Transverse restraining straps connected to the lower portion of the garment extend transversely to the longitudinal axis of the body of the wearer and connect to the bed or other supporting structure to inhibit movement of a sidewise nature.

8 Claims, 3 Drawing Figures

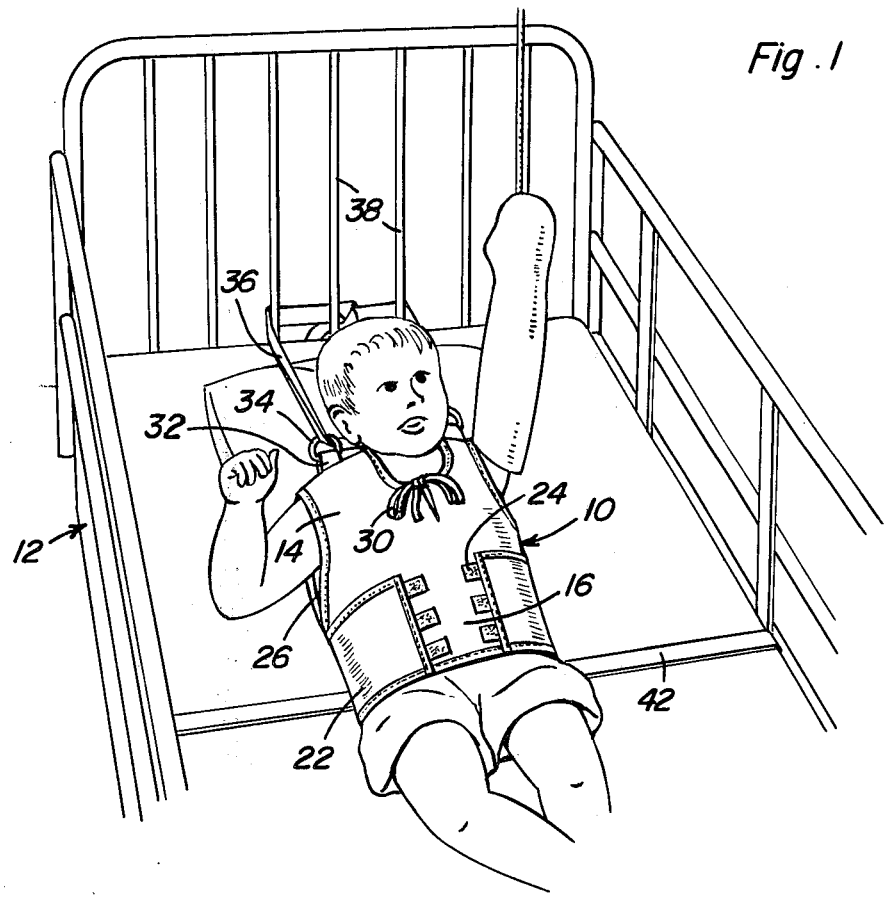
Fig. 1
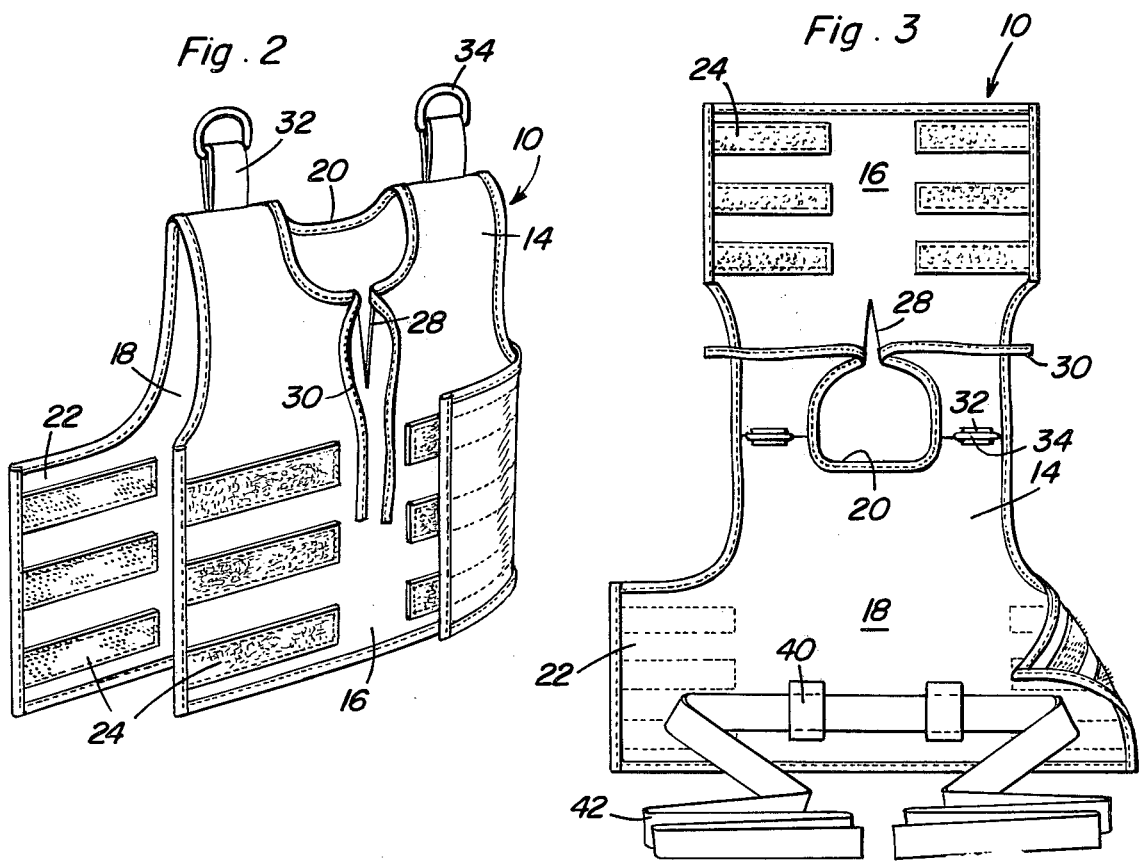
Fig. 2
Fig. 3

PEDIATRIC RESTRAINT GARMENT

BACKGROUND AND SUMMARY OF THE INVENTION

The present invention relates generally to restraining garments used to inhibit bodily motion of a wearer while in a bed, chair, transportable table, or other supporting structure. Garments similar to the present article of clothing have previously been provided to assist ill or injured individuals to remain on a supporting structure such as a bed. Such garments also have proven useful to some degree to prevent "unreliable" patients, such as young children, from leaving a bed or from moving in a fashion which would disrupt or render ineffective certain modes of treatment such as traction of a limb. In many such situations, injury to the patient can occur if certain movements are not restricted. These prior garments have included tubular restraint jackets which are difficult to fit over the head and arms of a wearer, especially when the movement of an arm is restricted due to a particular treatment modality. Prior restraint garments having open sides which facilitate placement of the garment on the wearer have also been proposed. However, no such garments of either type have been previously provided which are capable of restricting both transverse and longitudinal movements, relative to the bed or other supporting structure, of a wearer.

Restraint garments previously disclosed in the art and which are indicative of the background of the invention are described in the following U.S. Pat. Nos.: 1,573,446 Popham Feb. 16, 1926, 2,521,175 Kruse Sept. 5, 1950, 3,181,530 Storey May 4, 1965, 3,616,464 Whitter Nov. 2, 1971, 3,742,945 Reinhardt July 3, 1973, 3,788,309 Zeilman Jan. 29, 1974.

The present invention comprises a restraint garment formed basically of a one-piece panel structure which can be completely disposed around the upper torso of the body of a wearer. The one-piece panel structure is provided with an aperture located centrally of the structure which is of sufficient size to receive the head and neck of a wearer therethrough. On passage of the head and neck through the aperture, major portion of the panel structure lying adjacent the aperture and to the front and rear of the body of the wearer are draped respectively over the anterior and posterior portions of the torso. Lower portions of the panel structure overlying the waist of the wearer are fastened together to form a jacket-like encasement about the torso, the arms of the wearer fitting in arm holes formed on connection of the lower portions of the garment together. Straps connected to the upper portion of the garment near the neck of the wearer and extending longitudinally of the body of the wearer and to restrain movement longitudinally of the bed or other supporting structure. A separate set of straps is connected to the garment near the lower portion thereof and on the posterior surface thereof, the straps extending transversely of the body of a wearer to restrain movement of a sidewise nature. Both sets of straps connect to rails or other portions of the bed to hold the wearer under restraint.

Accordingly, it is an object of the invention to provide a restraining garment, the body of which is of uniform construction and which completely surrounds the upper torso of a wearer, the garment being adjustable to fit the contours of the wearer after placement on the wearer.

It is a further object of the invention to provide a motion-inhibiting garment for securing a child or medical patient to a bed or the like, whereby the garment can be draped over the body of the wearer and wrapped thereabout to form a jacket-like restraining garment with minimum disturbance to the limbs of the wearer.

It is another object of the invention to provide a restraint garment capable of inhibiting both longitudinal and transverse motion of a wearer, relative to a bed or other supporting structure, and wherein tensions on the garment are substantially accommodated without transference thereof to the body of the wearer.

These, together with other objects and advantages which will become subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view illustrating the present restraint garment in a use environment;

FIG. 2 is a perspective view of the main body portion of the present restraint garment; and, FIG. 3 is a plan view with certain elements of the structure shown in perspective of the present garment.

DESCRIPTION OF THE PREFERRED EMBODIMENT

Referring now to FIG. 1, the present restraint jacket is seen at 10 in a use environment. In the situation illustrated, a child suffering from a supracondylar fracture of the elbow has the affected arm suspended in traction over his bed 12. If the child were allowed freedom of movement either longitudinally, or transversely, to the major axis of the bed or perpendicular to the planar surface of the bed, the traction apparatus would become twisted thereby rendering the treatment ineffective and risking injury to the child. The situation illustrated, as well as many other treatment modalities, requires that motion be inhibited. The restraint jacket employed to accomplish this function, as will be described hereinafter relative to the present jacket 10, must be capable of being placed on the child or user without the requirement that one or both of the arms be fitted through intact arm holes. The present jacket 10 is also useful for simple restraint situations where the degree of freedom allowed to a child is to be restricted for safety reasons.

Referring also now to FIGS. 2 and 3, the jacket 10 is seen to comprise a panel member 14 which forms the body portion of the jacket. The panel member 14 can be formed of suitable "flat goods", such as fabric, etc., and can be patterned or colored for decorative enhancement. The panel member 14 has an anterior portion 16 and a posterior portion 18, a neck opening 20 being centrally located between the portions 16 and 18 to receive the head and neck of a user therethrough. The anterior portion 16 of the jacket 10 fits over the chest and other frontal portions of the upper torso. The posterior portion 18 of the jacket fits over and covers the back of the user. The posterior portion 18 of the jacket 10 broadens near the lower side edges thereof to form flap-like extensions or "wings" 22, the wings 22 being flexible extensions of the panel member 14. The inner surfaces of each of the wings 22 and portion of the outer surface of the anterior portion 16 of the panel member 14 have contact fasteners 24 formed in strips thereon, the strips mating when the wings 22 are folded around the side of the user and over the outer surface of the anterior portion 16. The contact fasteners 24 can preferably be that type of fastening closures comprised of nylon tapes having naps or piles formed of myriad small fiber loops and fiber hooks. Such material is commercially available an is marketed under the trademark "Velcro". While this type of material can conveniently be used, the present jacket is not limited thereto.

Thus, the planar panel member 14 forms arm holes 26 when the wings 22 are drawn over the lower frontal portions of said member 14 and fastened thereto. The neck opening 20 can be formed with a V-like slit 28 formed in the anterior portion 16 of the panel member 14, the slit 28 enlarging the opening 20 as necessary. The slit 28 can then be tied off to fit the neck of a user by means of simple tie laces 30 joined to opposed edges of the juncture of the opening 20 and the slit 28.

That portion of the panel member 14 which fits over and covers the shoulder of a user, i.e., the portion of the member 14 between the anterior portion 16 and posterior portion 18 and spaced laterally from the neck opening 20, has flexible loops 32 attached in lateral alignment and extending outwardly from the outer surface of the panel member 14. D-rings 34, which can be formed of rigid materials such as metal, plastic, or the like, are held within and by the loops 32. The rings 34 receive a flexible strap or shoulder belt 36 therethrough, the belt 36 being drawn through both of the rings 34 and fitted about railings 38 at the head of the bed 12. While the ends of the belt 36 could be tied to the railings 38, the belt 36 can more effectively be utilized by tying said belt into a loop encompassing one or more of the vertical railings 38.

The outer surface of the anterior portion 18 of the panel member 14 near the portion thereof which fits over the small of the back of a user when worn has two aligned belt loops 40 formed thereon, the opening of the loops 40 being aligned laterally of the panel member 14. A waist belt 42 is drawn through the loops 40, the ends of the belt 42 extending to opposite lateral edges of the bed 12 and being fastened to the bed. The belt 42 can be wrapped and tied about the mattress on the bed 12 or can be fastened to rails or other structure along the lateral edges of the bed 12.

The shoulder belt 36 acts to secure the wearer of the jacket 10 from sitting up or moving sideways in the bed 12. The waist belt 42 prevents the wearer from turning upside down or moving sideways in the bed 12. In effect, the shoulder belt 36 and waist belt 42 inhibit longitudinal and transverse motions, as well as motion normal to the surface of the bed 12, with minimum transfer of force to the body of the user. Thus, the present jacket 10 can safely be worn by a child whose movements must be inhibited during medical treatment or for other consideration of safety.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A restraint garment for at least partially inhibiting the movements of a person on a supporting structure, comprising:

a flexible panel member having anterior and posterior portions, the panel member having an opening formed centrally therein between said anterior and posterior portions, the opening receiving the head and neck of a user, the anterior and posterior portions of the panel member respectively fitting over and generally loosely conforming to the frontal surfaces and rear surfaces of the upper torso of said user;

flap-like wing members extending laterally from each side of the posterior portion of the panel member;

contact fastening means disposed on inner surfaces of the wing members and on outer surfaces of the lower portions of the anterior portion of the panel member, the fastening means mating and connecting together on folding of the wing members over and into engagement with the lower portions of the anterior portion of the panel member, thereby to secure the panel member about the upper torso of the user;

shoulder belt means connected to the panel member near the opening and extending longitudinally of the body of the user to connection with the supporting structure; and, waist belt means connected to the panel member at lower portions of the posterior portion of the panel member and extending transversely of the body of the user to connection with the supporting structure.

2. The restraint garment of claim 1 wherein the panel member has shoulder portions located about the opening and between the anterior and posterior portions of the panel member, the shoulder portions fitting over the shoulders of a user, the garment further comprising;

flexible loop means attached to the shoulder portion; and rigid ring means being partially received by and held within said loop means, the shoulder belt means being threaded through said ring means, the belt means being movable within and through said ring means.

3. The restraint garment of claim 2 and further comprising:

second loop means attached to the outer surface of the posterior portion of the panel member, the openings of the second loop means being aligned transversely of the body of a user, the waist belt means being threaded through the second loop means and being movable therein.

4. The restraint garment of claim 3 wherein the anterior portion of the panel member has a slit formed therein, the slit communicaing with the neck opening; and, tie lace means attached to oppositely spaced edges of the panel member defining said slit at the juncture of the slit and the opening.

5. A garment, comprising:

a flexible panel member having anterior and posterior portions, the panel member having an opening formed therein for receiving the head and neck of a user, at least portions of the anterior an posterior portions of the panel member respectively fitting over and generally loosely conforming to the frontal surfaces and rear surfaces of the upper torso of said user; and, contact fastening means disposed on inner surfaces of one of the said portions and on outer surfaces of the other of said portions of the panel member for mating and connecting together said portions on folding of the portions over and into engagement with each other, thereby to secure the panel member about the upper torso of the user.

6. The garment of claim 5 and further comprising:
flap-like wing members extending laterally from each side of one of said portions of the panel member, the contact fastening means being disposed on the wing members on one surface thereof, the fastening means mating and connecting together on folding of the wing members over and into engagement with the lower portions of the other portion of the panel member.

7. The garment of claim 5 and further comprising:
belt means connected to the panel member for connecting the garment with a support structure.

8. The garment of claim 7 wherein the belt means comprise:
shoulder belt means connected to the panel member near the opening and extending longitudinally of the body of the user; and,
waist belt means connected to the panel member at lower portions of the posterior portion of the panel member and extending transversely of the body of the user.

* * * * *